US011992608B2

(12) United States Patent
Säll (10) Patent No.: US 11,992,608 B2
(45) Date of Patent: May 28, 2024

(54) LOCKING MECHANISM FOR AN AEROSOL DISPENSER

(71) Applicant: SHL MEDICAL AG, Zug (CH)

(72) Inventor: Daniel Säll, Segeltorp (SE)

(73) Assignee: SHL MEDICAL AG, Zug (CH)

( * ) Notice: Subject to any disclaimer, the term of this patent is extended or adjusted under 35 U.S.C. 154(b) by 667 days.

(21) Appl. No.: 17/275,613

(22) PCT Filed: Sep. 12, 2019

(86) PCT No.: PCT/EP2019/074315
§ 371 (c)(1),
(2) Date: Mar. 11, 2021

(87) PCT Pub. No.: WO2020/064343
PCT Pub. Date: Apr. 2, 2020

(65) Prior Publication Data
US 2022/0047823 A1 Feb. 17, 2022

(30) Foreign Application Priority Data

Sep. 27, 2018 (EP) .................................... 18197317

(51) Int. Cl.
*A61M 15/00* (2006.01)
*A61F 9/00* (2006.01)
*B05B 11/10* (2023.01)
(52) U.S. Cl.
CPC ....... *A61M 15/0081* (2014.02); *A61F 9/0008* (2013.01); *A61M 15/0071* (2014.02); *B05B 11/108* (2023.01); *B05B 11/1091* (2023.01)
(58) Field of Classification Search
CPC .............. A61M 15/00; A61M 15/0001; A61M 15/0065; A61M 15/0068; A61M 15/007;
(Continued)

(56) References Cited

U.S. PATENT DOCUMENTS 5,964,416 A * 10/1999 Jaeger ................. B05B 11/1067
222/402
6,149,054 A * 11/2000 Cirrillo ................... G01F 11/00
235/34
(Continued)

FOREIGN PATENT DOCUMENTS

EP 2835146 A1 2/2015
JP 2016-527040 A 9/2016
(Continued)

OTHER PUBLICATIONS

International Search Report and Written Opinion for Int. App. No. PCT/EP2019/074315, mailed Dec. 13, 2019.

*Primary Examiner* — Colin W Stuart
(74) *Attorney, Agent, or Firm* — McDonnell Boehnen Hulbert & Berghoff LLP (57) ABSTRACT

A locking mechanism for an aerosol dispenser is presented having a first body structure, a second body structure rotatably attached to the first body structure, a spindle rotatably attached to the second body structure, the spindle having an actuator rotationally cooperating with the first body structure such that rotation of the first body structure relative to the second body structure causes rotation of the actuator and of the spindle, a movable element arranged around the spindle, the spindle being rotatable relative to the movable element, wherein rotation of the spindle causes movement of the movable element along the spindle from an initial position to a final position, and a locking element, wherein in the final position the movable element applies a radial force onto the locking element causing the locking element to bend in the radial direction thereby preventing rotation between the first body structure and the second body structure.

12 Claims, 7 Drawing Sheets

(58) Field of Classification Search
CPC .......... A61M 15/0071; A61M 15/0073; A61M 15/0075; A61M 15/0076; A61M 15/0078; A61M 15/0081; A61M 2205/27; A61M 2205/273; A61M 2205/276
See application file for complete search history.

(56) References Cited

U.S. PATENT DOCUMENTS

| | | |
|---|---|---|
| 7,396,341 B2 | 7/2008 | Schyra et al. |
| 2004/0094147 A1 | 5/2004 | Schyra et al. |
| 2013/0125880 A1* | 5/2013 | Holakovsky ........ B05B 11/0054 128/200.21 |
| 2017/0157345 A1* | 6/2017 | Panjabi ............. A61M 15/0071 |

FOREIGN PATENT DOCUMENTS

| | | | |
|---|---|---|---|
| WO | 93/21980 A1 | 11/1993 | |
| WO | 96/21980 A1 | 7/1996 | |
| WO | 2007/22898 A2 | 3/2007 | |
| WO | WO-2012160052 A1 * | 11/2012 | .......... A61M 11/007 |
| WO | 2015/018903 A1 | 2/2015 | |

* cited by examiner

Fig. 9

LOCKING MECHANISM FOR AN AEROSOL DISPENSER

CROSS REFERENCE TO RELATED APPLICATIONS

The present application is a U.S. National Phase Application pursuant to 35 U.S.C. § 371 of International Application No. PCT/EP2019/074315 filed Sep. 12 2019, which claims priority to European Patent Application No. 18197317.3 filed Sep. 27, 2018. The entire disclosure contents of these applications are herewith incorporated by reference into the present application.

TECHNICAL FIELD

The present disclosure generally relates to aerosol dispensers.

BACKGROUND

Aerosol dispensers may be configured to provide multiple doses of a liquid such as a medicament. In certain applications, for example in medicament applications, it is important to ensure that the user receives the dispensed dose. Therefore, in case that the liquid cartridge is empty, this should preferably be indicated to the user such that the user does not attempt to use an empty aerosol dispenser. The user could in such cases without further aids be left with the impression that liquid has been dispensed, since the dose is generally very small and the liquid forms an aerosol during dispensing. It may therefore be difficult for a user to detect whether liquid has in fact been dispensed. One measure to enable a user to identify that the liquid cartridge is empty is by setting the empty aerosol dispenser in a state in which the user is unable to trigger liquid dispensing.

U.S. Pat. No. 7,396,341 B2 discloses an inhaler which is provided with a blocking device. The inhaler has a locking-stressing-mechanism with spring-actuated output drive and a counter, accommodated in a two-part housing. The two parts are mounted to be rotatable relative to each other, and can be blocked by means of a pre-stressed leaf spring. The leaf spring is initially accommodated in a recess in the wall of one housing part. As soon as the permitted number of actuations has been reached a push rod pushes the leaf spring out of its resting position. The leaf spring then jumps into a recess in the wall of the other housing part and the two housing parts can no longer be rotated relative to each other.

One drawback with the configuration disclosed in U.S. Pat. No. 7,396,341 B2, is that it may make assembly as well as the design of the inhaler more complex.

SUMMARY

In view of the above, a general object of the present disclosure is to provide a locking mechanism for an aerosol dispenser which solves or at least mitigates problems of the prior art.

There is hence according to a first aspect of the present disclosure provided a locking mechanism for an aerosol dispenser, wherein the locking mechanism comprises: a first body structure, a second body structure configured to be rotatably attached to the first body structure, a spindle configured to be rotatably attached to the second body structure, the spindle having an actuator configured to rotationally cooperate with the first body structure such that rotation of the first body structure relative to the second body structure causes rotation of the actuator and of the spindle, a movable element arranged around the spindle, the spindle being rotatable relative to the movable element, wherein rotation of the spindle causes movement of the movable element along the spindle from an initial position to a final position, and a locking element, wherein in the final position the movable element is configured to apply a radial force onto the locking element causing the locking element to bend in the radial direction thereby preventing rotation between the first body structure and the second body structure.

The first body structure and the second body structure may thereby become rotationally locked relative to each other when the movable element reaches its final position. This may in particular be obtained without the use of a pre-stressed leaf spring actuated by axial movement of a push rod, which is the case in U.S. Pat. No. 7,396,341 B2. The locking mechanism may thereby be made more robust and assembly of the locking mechanism and of the aerosol dispenser may be simplified.

The movable element may be configured to move a predefined distance along the spindle for each dispensing operation. The movable element is hence configured to move incrementally towards the final position. The final position may correspond to a total number of permitted dispensing operations.

According to one embodiment in the final position the locking element is configured to engage with both the first body structure and the second body structure, thereby causing rotational interlocking of the first body structure and the second body structure.

According to one embodiment the locking element is arranged in a first recess of a wall and attached to the wall of one of the first body structure and the second body structure.

According to one embodiment the movable element is configured to axially slide against the locking element as the movable element is moved towards the final position to thereby bend the locking element radially such that it engages with a second recess of a wall of the other one of the first body structure and the second body structure.

According to one embodiment the movable element is a dose indicator configured to provide an indication of the remaining number of doses.

According to one embodiment the locking element is a spring.

According to one embodiment the spring is a sheet spring.

According to one embodiment the spindle and the movable element have a threaded connection.

According to one embodiment the movable element has an elongated axially extending end portion which has a bevelled cross-section, and wherein the locking element has a radially curved section configured to cooperate with the axially extending end portion to thereby cause bending of the locking element.

There is according to a second aspect of the present disclosure provided a locking mechanism for an aerosol dispenser, wherein the locking mechanism comprises: a first body structure, a second body structure configured to be rotatably attached to the first body structure, a spindle configured to be rotatably attached to the second body structure, the spindle having an actuator configured to rotationally cooperate with the first body structure such that rotation of the first body structure relative to the second body structure causes rotation of the actuator and of the spindle, a movable element arranged around the spindle, the spindle being rotatable relative to the movable element, wherein rotation of the spindle causes movement of the movable element along the spindle from an initial position to a final position, wherein the movable element is configured to engage with the first body structure in the final position to thereby prevent rotation of the first body structure relative to the second body structure.

The first body structure and the second body structure may thereby become rotationally locked relative to each other when the movable element reaches its final position. This may in particular be obtained in a simplified manner, since no pre-stressed leaf spring is required to perform the interlocking. The locking mechanism may thereby be made more robust and assembly of the locking mechanism and of the aerosol dispenser may be simplified.

According to one embodiment the movable element has an axially extending end portion configured to engage with an axial recess of the first body structure when the movable element is in the final position to prevent rotation of the first body structure relative to the second body structure.

According to one embodiment the movable element is a dose indicator configured to provide an indication of the remaining number of doses.

According to one embodiment the spindle and the movable element have a threaded connection.

There is according to a third aspect of the present disclosure provided a locking mechanism according to the first aspect.

According to one embodiment the aerosol dispenser is an inhaler or an eye dispenser.

Generally, all terms used in the claims are to be interpreted according to their ordinary meaning in the technical field, unless explicitly defined otherwise herein. All references to "a/an/the element, apparatus, component, means, etc. are to be interpreted openly as referring to at least one instance of the element, apparatus, component, means, etc.", unless explicitly stated otherwise.

BRIEF DESCRIPTION OF THE DRAWINGS

The specific embodiments of the inventive concept will now be described, by way of example, with reference to the accompanying drawings, in which.

DETAILED DESCRIPTION

The inventive concept will now be described more fully hereinafter with reference to the accompanying drawings, in which exemplifying embodiments are shown. The inventive concept may, however, be embodied in many different forms and should not be construed as limited to the embodiments set forth herein; rather, these embodiments are provided by way of example so that this disclosure will be thorough and complete, and will fully convey the scope of the inventive concept to those skilled in the art. Like numbers refer to like elements throughout the description.

Figures 1, 2A:
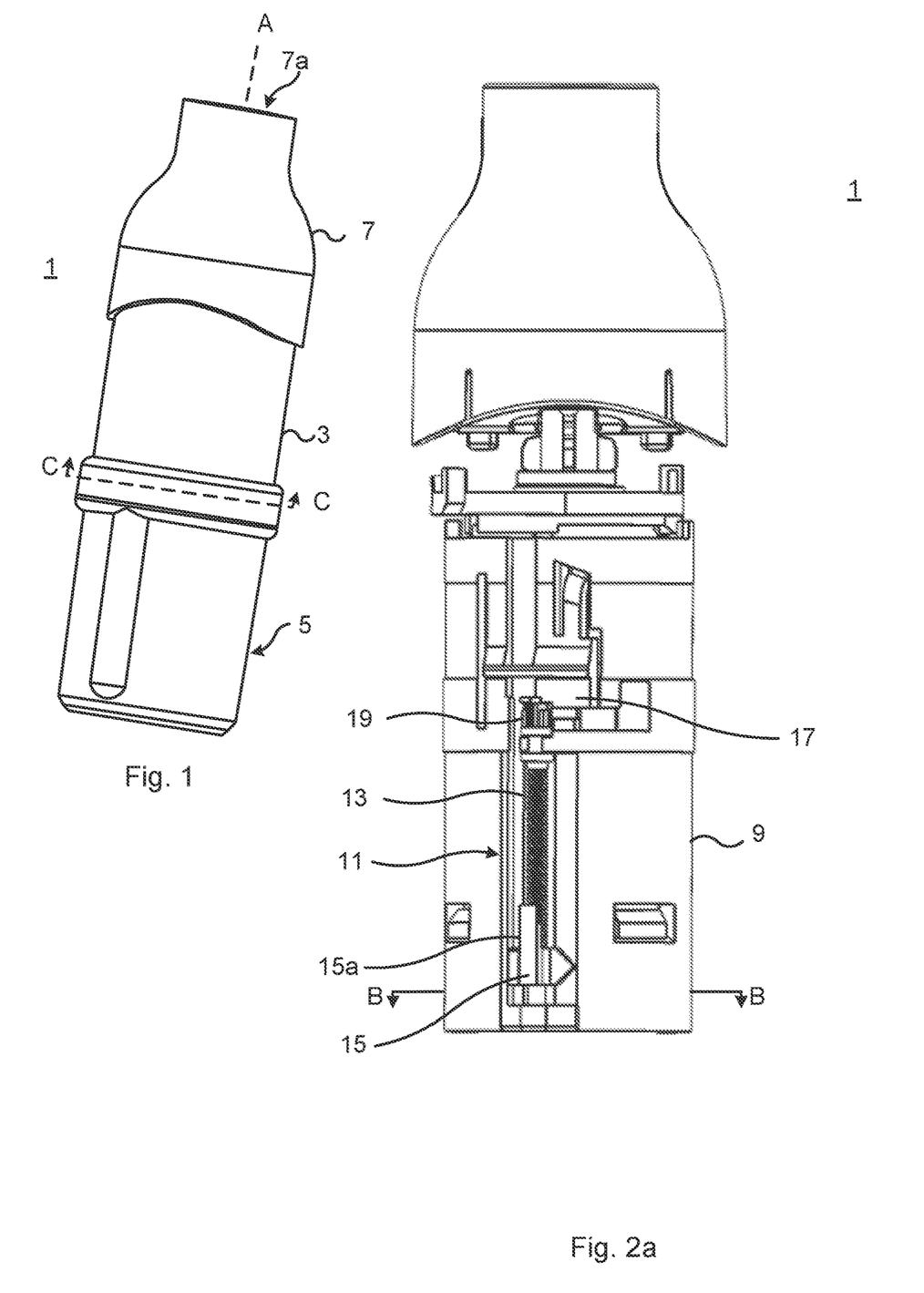
FIG. 1 shows a perspective view of one example of an aerosol dispenser.
FIG. 2a shows the interior of an aerosol dispenser.

FIG. 1 shows a perspective view of an example of an aerosol dispenser 1. The aerosol dispenser 1 comprises a first body structure 3 and a housing member 5. The first body structure 3 forms part of an external housing of the aerosol dispenser 1. The housing member 5 also forms part of the external housing of the aerosol dispenser 1.

In the example in FIG. 1, the first body structure 3 and the housing member 5 have an elongated shape and are coaxially arranged. The central axis A of each of the first body structure 3 and the housing member 5 coincide and form the central axis of the aerosol dispenser 1.

The exemplified aerosol dispenser 1 furthermore comprises an aerosol dispensing end member 7 attached to the first body structure 3. The aerosol dispensing end member 7 forms an aerosol dispensing end of the aerosol dispenser 1. The aerosol dispensing end member 7 is provided with an opening 7a through which an aerosol may be dispensed.

In the example shown in FIG. 1, the housing member 5 forms a distal end of the aerosol dispenser 1 and the aerosol dispensing end member 7 forms a proximal end of the aerosol dispenser 1. The first body structure 3 is arranged axially between the housing member 5 and the aerosol dispensing end member 7.

The first body structure 3 is configured to be rotatably attached to the housing member 5. In particular, the aerosol dispenser 1 is configured to be activated by rotation of the housing member 5 relative to the first body structure 3. This rotation may for example be about 180 degrees. Thus, every time that the aerosol dispenser 1 is activated for a dispensing operation the housing member 5 is rotated a predetermined amount relative to the first body structure 3. A trigger, not shown in FIG. 1, is configured to trigger the aerosol dispensing operation when the aerosol dispenser 1 has been activated.

FIG. 2a shows the aerosol dispenser 1 with the first body structure 3 and the housing member 5 removed. The aerosol dispenser 1 furthermore comprises a second body structure 9 in the form of an inner sleeve configured to be arranged radially inwards of and concentrically with the housing member 5. The second body structure 9 is configured to receive a cartridge such as a medicament cartridge. The second body structure 9 and the housing member 5 are rotationally locked relative to each other.

The aerosol dispenser 1 comprises a locking mechanism 11 for rotationally locking the first body structure 3 and the second body structure 9 relative to each other when all the doses have been dispensed from the cartridge, to thereby prevent activation of the aerosol dispenser 1 when no further doses are available. The locking mechanism 11 includes the first body structure 3, the second body structure 9, a spindle 13, a movable element 15, a locking element 17, and an actuator 19.

The spindle 13 is rotatably attached to the second body structure 9. The spindle 13 extends parallel with the central axis A along the outer surface of the second body structure 9. The spindle 13 is provided with threads.

The movable element 15 may be a dose indicator. The movable element 15 is configured to be arranged on the spindle 13. The spindle 13 and the movable element 15 have 
a threaded connection. The movable element 15 is in an initial position at a distal end of the spindle 13 as long as no doses have been dispensed from the aerosol dispenser 1. The spindle 13 is configured to rotate a predefined amount with each dispensed dose. The movable element 15 is thereby moved incrementally along the spindle 13 to indicate the number of doses left. The movable element 15 is configured to move along the spindle 13 from the initial position towards a final position, in which no further doses are available. As an example, the aerosol dispenser 1 may be designed to deliver 30 or 60 doses, and thus with each dispensed dose, the movable element 15 is moved ⅟30 or ⅟60 of the length between the initial position and the final position.

Figure 3:
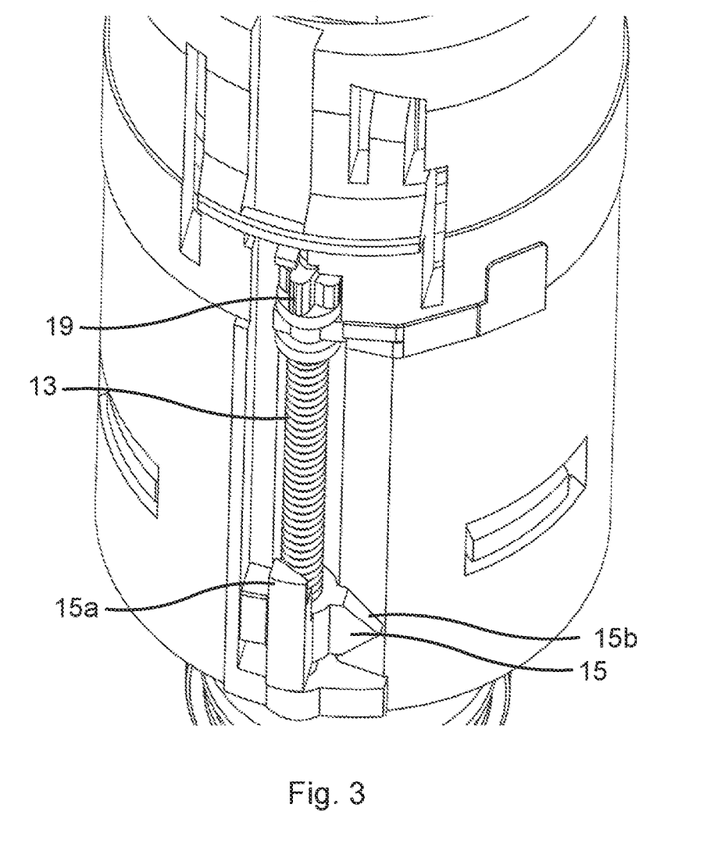
FIG. 3 shows a perspective view of an example of a locking mechanism of the aerosol dispenser in FIG. 1.

The movable element 15 may be provided with an elongated axially extending end portion 15a, which extends towards the actuator 19. The axially extending end portion 15a may be bevelled in cross-section, i.e. a section perpendicular to the central axis A, as shown in FIG. 3. The axially extending end portion 15a is configured to cooperate with the locking element 17 when the movable element 15 is about to move into the final position, as will be explained in more detail in what follows. The locking element 17 is radially flexible. The locking element 17 may be a spring such as a sheet spring. The locking element 17 may preferably be made of metal such as steel, aluminium or copper.

The actuator 19 is provided at one end of the spindle 13. The actuator 19 is rotatably fixed relative to the spindle 13. The actuator 19 may be integral with the spindle 13. The actuator 19 may for example be a cogwheel or have a cogwheel-like structure. Since the spindle 13 and the actuator 19 are rotatably fixed relative to each other, rotation of the actuator 19 results in that the spindle 13 is also rotated. The inner wall of the first body structure 3 may be provided with a radial structure 21, shown in FIG. 4, which is configured to cooperate with the actuator 19 when the housing member 5 is being rotated relative to the first body structure 3 and thus relative to the second body structure 9. The radial structures 21 may be designed such that the actuator 19 is rotated a predetermined amount, for example half a turn, every time the housing member 5 is rotated relative to the first body structure 3 to an activation position in which the aerosol dispenser 1 is activated.

Figure 2B:
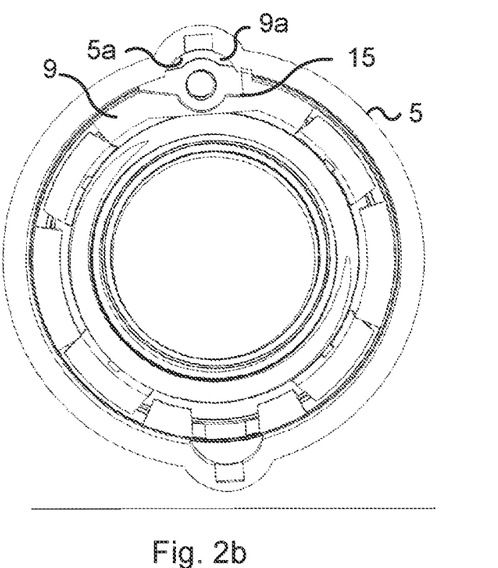
FIG. 2b shows a cross-section of the aerosol dispenser in FIG. 2a along lines B-B with the housing member attached.

FIG. 2b shows a cross-section along lines B-B, with the addition that the housing member 5 is provided around the second body structure 9. The housing member 5 has a radial recess 5a extending axially along its inner surface along the length of the spindle 13. A distal end portion of the second body structure 9 has a corresponding radially outwards extending protrusion 9a configured to be received by the radial recess 5a to thereby radially interlock the second body structure 9 and the housing member 5. An additional pair of such cooperating radially outwards extending protrusions and radial recess may be provided offset at for example about 180 degrees, as shown in FIG. 2b. The movable element 15 may be configured to run in the axially extending radial recess 5a. The movable element 15 is prevented from rotation due to its position in the axially extending radial recess 5a, causing it to move along the spindle 13 when the spindle 13 is being rotated.

FIG. 3 shows a close-up view of the aerosol dispenser 1 in FIG. 2a. In particular, the configuration of the movable element 15 is better visible. The movable element 15 has a dose indicating portion 15b, which may have a pointed shape. The dose indicating portion 15b may be configured to point towards a dose scale which may be arranged on the second body structure 9. Hereto, the housing member 5 may have a window in the region of the spindle 13 or it may be transparent to provide visibility of the movable element 15.

Figure 4:
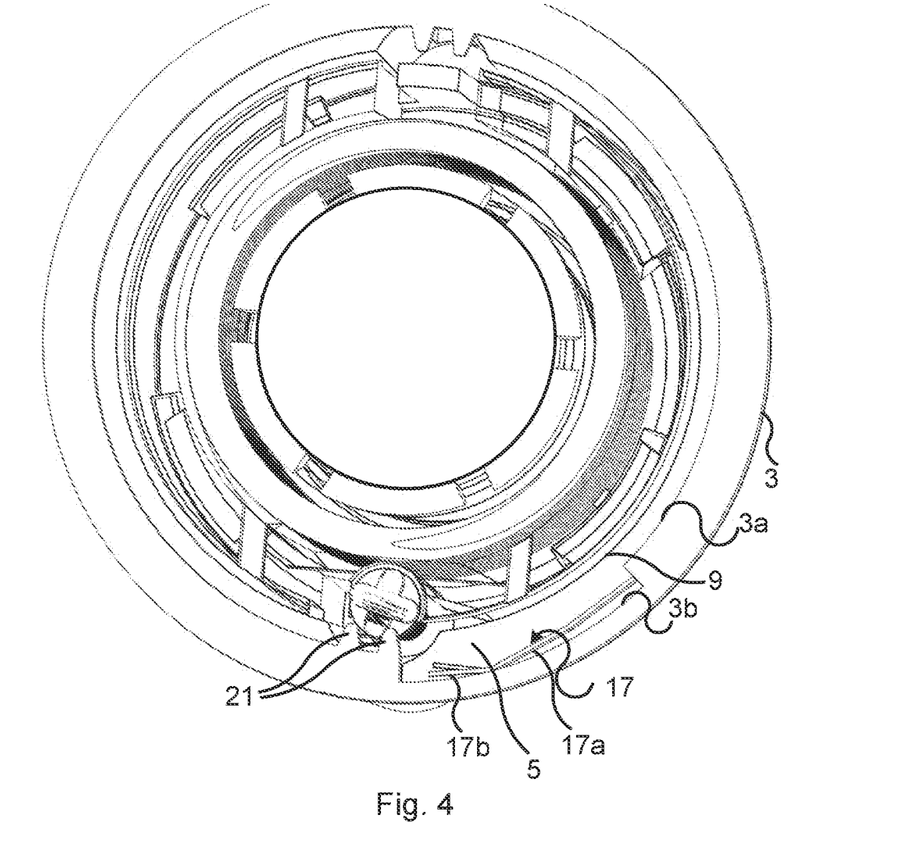
FIG. 4 is a cross-section along lines C-C in FIG. 1 when the aerosol dispenser is able to dispense a dose.
Figure 5:
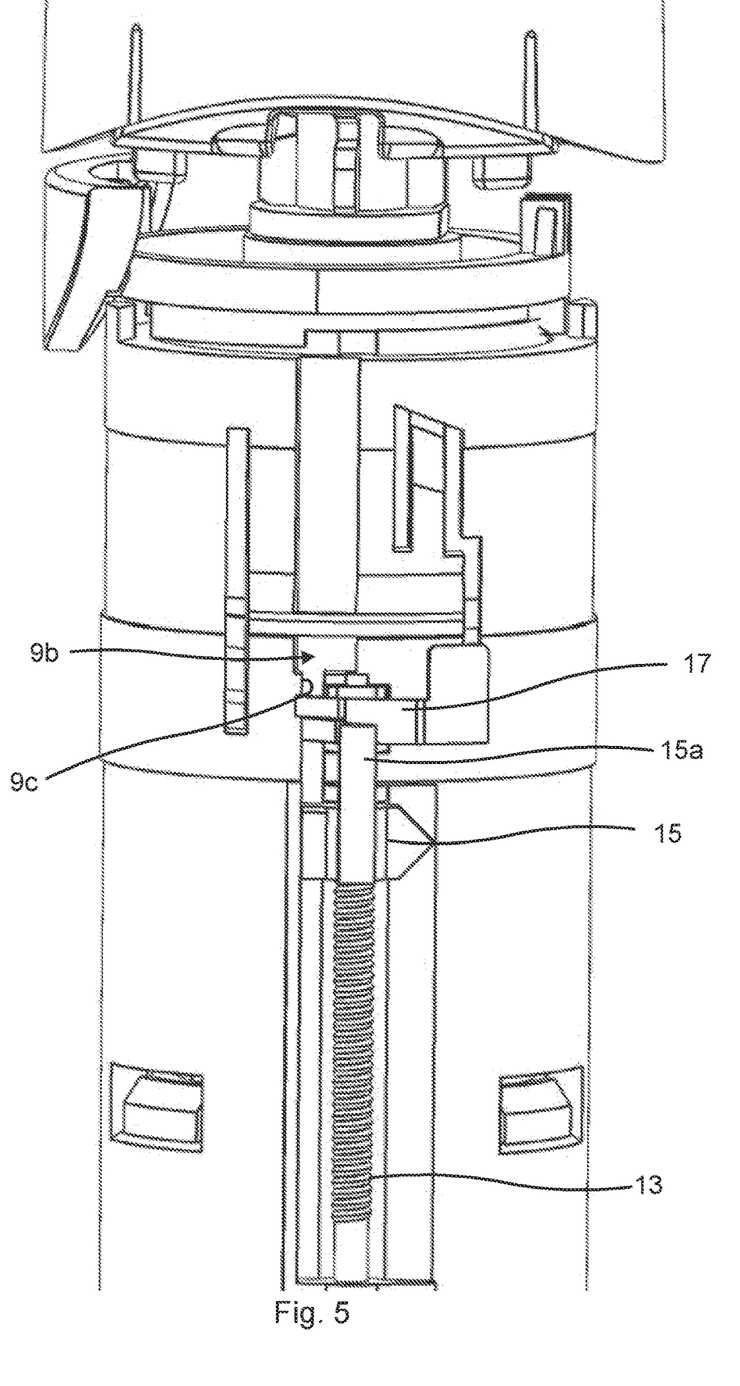
FIG. 5 shows the aerosol dispenser in FIG. 2 when a movable element is in a final position.
Figure 6:
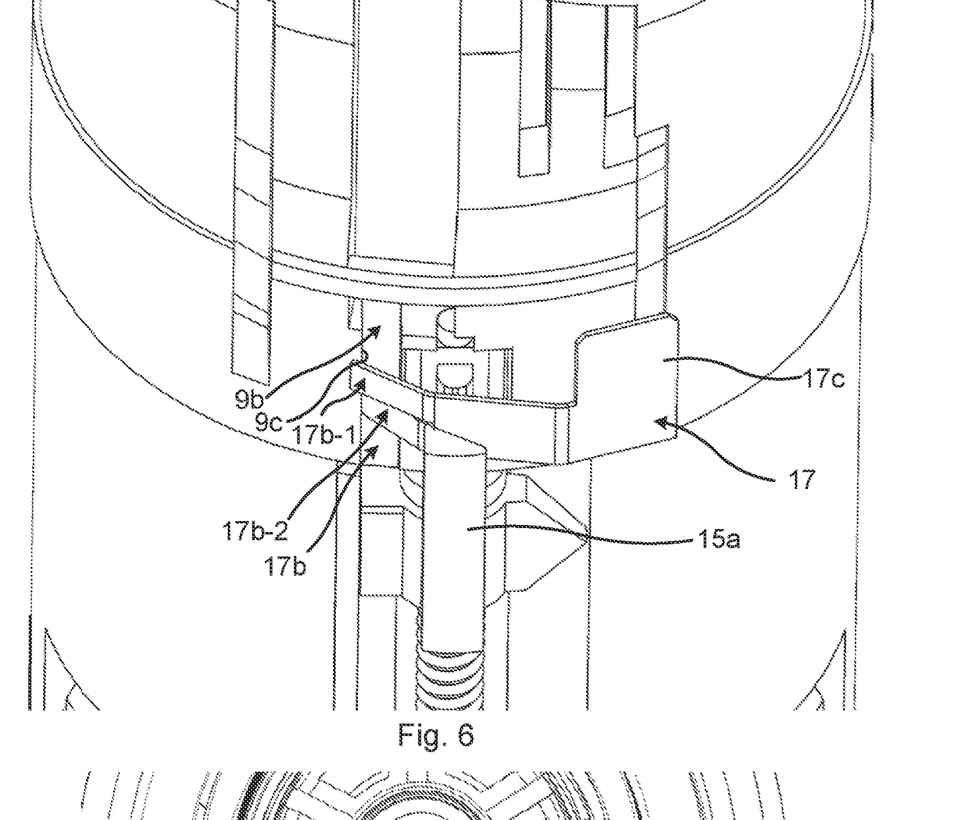
FIG. 6 shows the aerosol dispenser in FIG. 2 when a movable element is in a final position.
Figure 7:
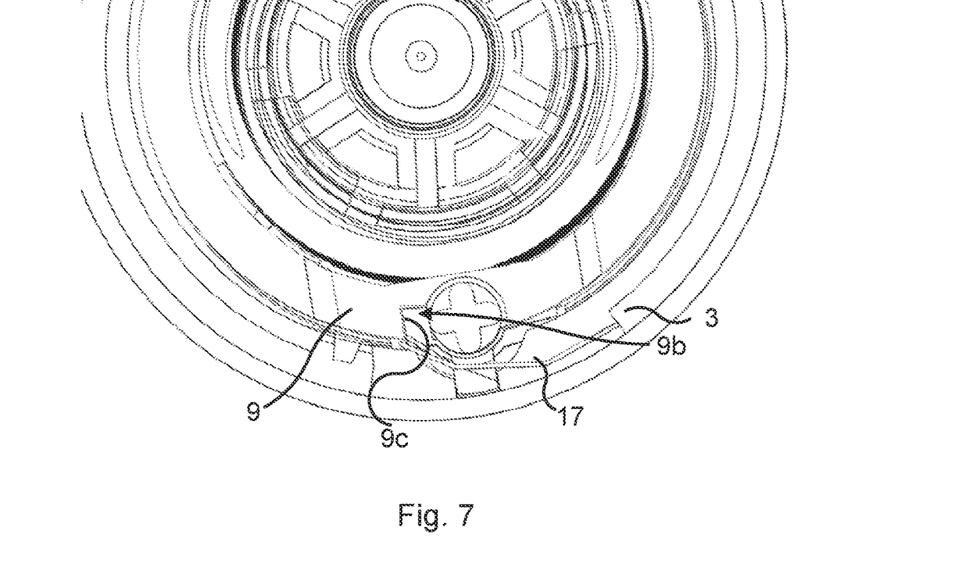
FIG. 7 shows a cross-section along lines C-C when the movable element is in the final position.

FIG. 4 shows a cross-section along lines C-C in FIG. 1 when the aerosol dispenser 1 still contains one or more doses and prior to activation of the aerosol dispenser 1. The first body structure 3 has an inner wall 3a provided with a first recess 3b. The locking element 17 which has an elongated structure is arranged in the first recess 3b. The locking element 17 may be fixed to the first body structure 3 in the first recess 3b at one element 17. The chamfered design of the axially extending end portion 15*a* facilitates for the movable element 15 to slide beside the locking element 17 and bend the locking element 17 radially inwards. FIG. 7 shows a cross-section of the configuration depicted in FIG. 6.

As an alternative to the above-described configuration, the locking element could be attached to the second body structure, for example in the second recess. The axially extending end portion of the movable element could in this case bend the locking element radially outwards such that the locking element engages with the first radial recess of the first body structure when the movable element is in the final position.

Figure 8:
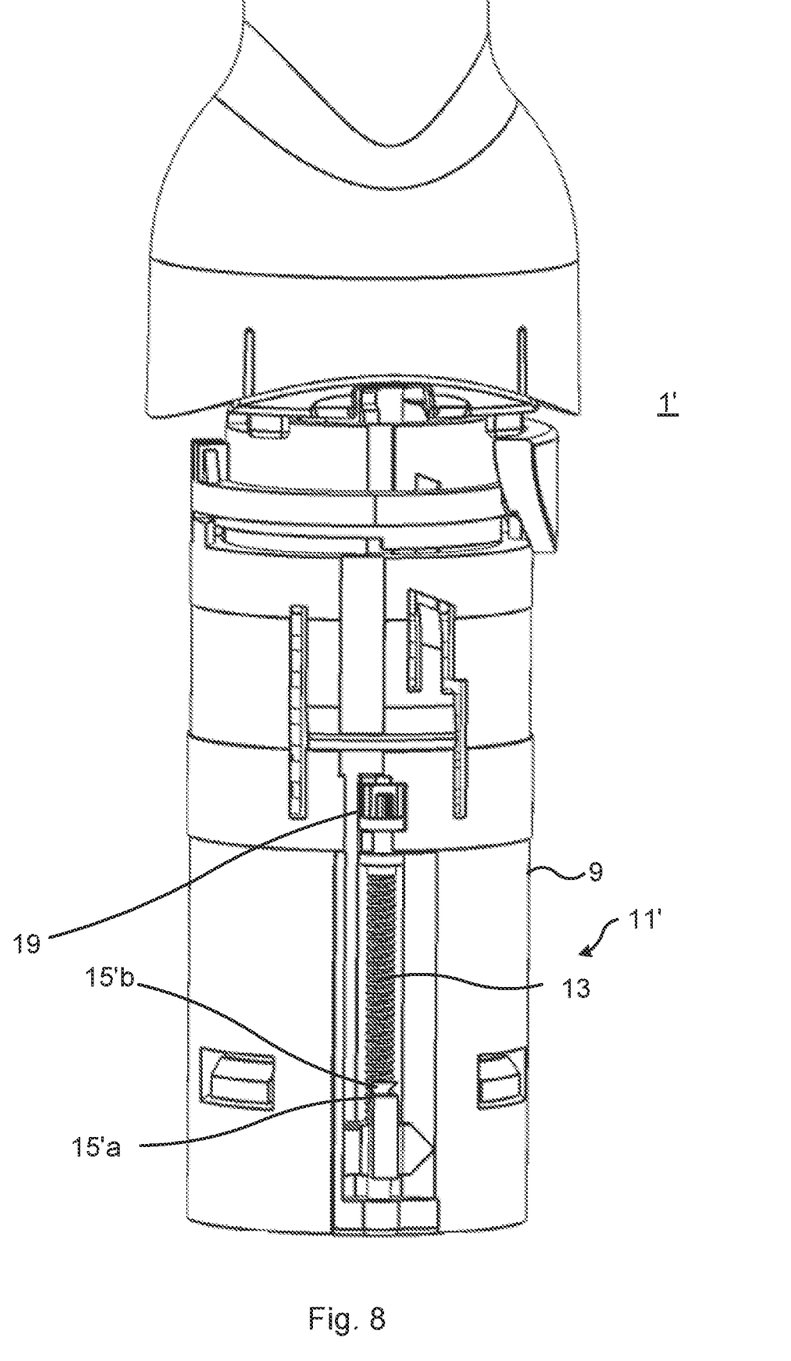
FIG. 8 shows another example of an aerosol dispenser with a movable element in an initial position.

FIG. 8 shows aerosol dispenser 1' provided with a variation of the locking mechanism. The locking mechanism 11' comprises a first body structure 3', which is very similar to the first body structure 3, the second body structure 9, the spindle 13, the actuator 19, and a movable element 15'. The spindle 13 and the actuator 19 function in the same manner as has previously been described.

The movable element 15' has an identical operation to the movable element 15 concerning its movement along the spindle 13. The movable element 15' has an axially extending end portion 15'*a* provided with a reinforced end such as a metal end 15'*b*.

Figure 9:
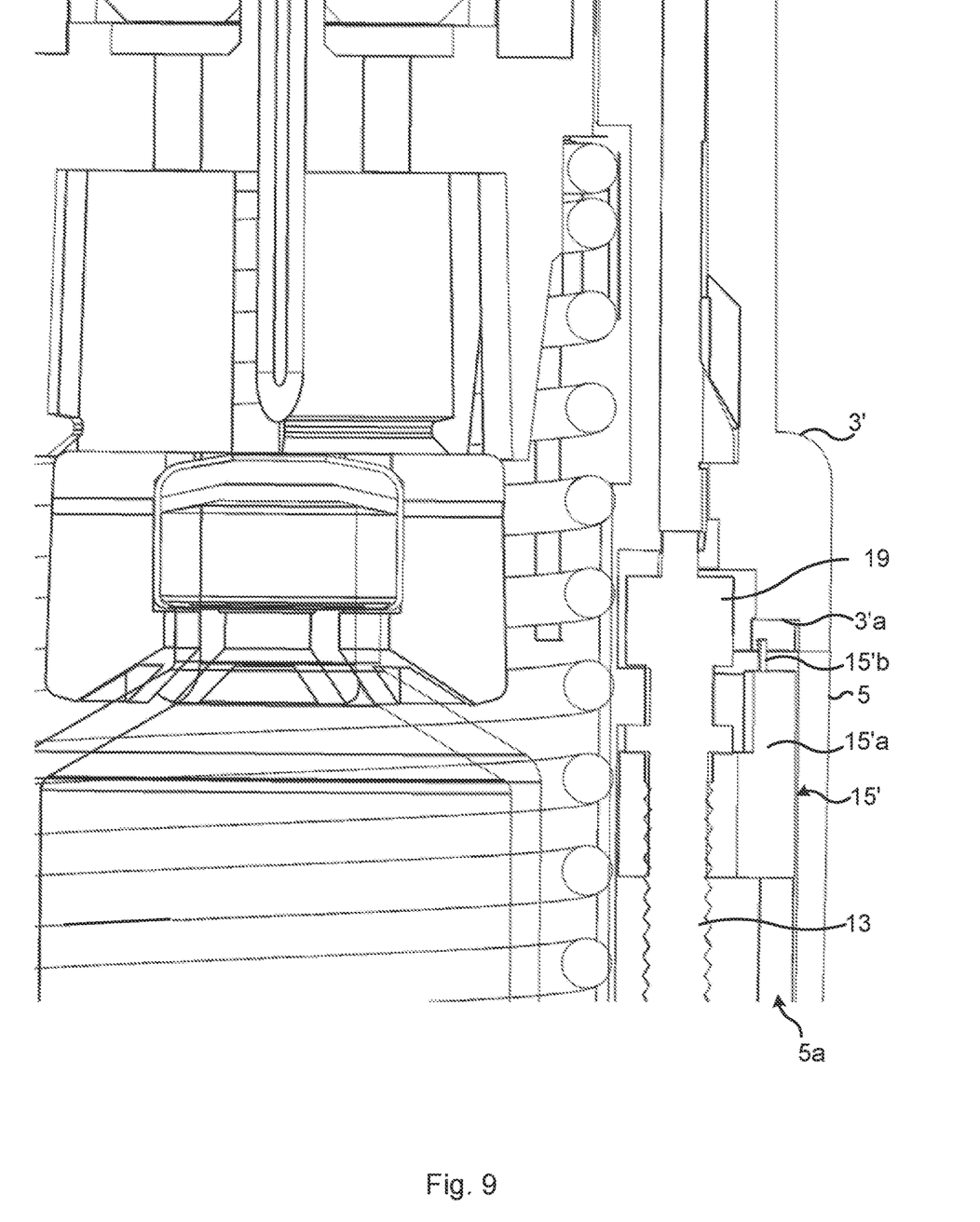
FIG. 9 shows a close-up of a longitudinal section of the aerosol dispenser in FIG. 8 when the movable element is in the final position.

In FIG. 8, the movable element 15' is in the initial position. FIG. 9 shows a longitudinal section of the aerosol dispenser 1 when the movable element 15' is in the final position. The first body structure 3' has an axial recess 3'*a*. The axial recess 3'*a* may be aligned with and form a continuation of the radial recess 5*a* of the housing member 5. The axial recess 3'*a* is configured to receive the movable element 15'. In particular, the axial recess 3'*a* is configured to receive the reinforced end 15'*b* of the movable element 15'. The movable element 15' is hence configured to engage with the first body structure 3' in the final position. Since the movable element 15' is arranged on the spindle 13, which is attached to the second body structure 9, the second body structure 9 becomes rotationally locked relative to the first body structure 3' when the movable element 15' is engaged with the first body structure 3'. The housing member 5 is rotatably fixed relative to the second body structure 9 and thus the housing member 5 also becomes rotationally locked relative to the first body structure 3'. Activation of the aerosol dispenser 1' is thereby prevented when the movable element 15' has reached the final position. Activation of the aerosol dispenser 1' is hence prevented when all of the doses have been used.

The inventive concept has mainly been described above with reference to a few examples. However, as is readily appreciated by a person skilled in the art, other embodiments than the ones disclosed above are equally possible within the scope of the inventive concept, as defined by the appended claims.

The invention claimed is:

1. A locking mechanism for an aerosol dispenser, wherein the locking mechanism comprises:
   a first body structure,
   a second body structure configured to be rotatably attached to the first body structure,
   a spindle configured to be rotatably attached to the second body structure,
   the spindle having an actuator configured to rotationally cooperate with the first body structure such that rotation of the first body structure relative to the second body structure causes rotation of the actuator and of the spindle,
   a movable element arranged around the spindle, the spindle being rotatable relative to the movable element, wherein rotation of the spindle causes movement of the movable element along the spindle from an initial position to a final position, and
   a locking element, wherein the locking element is arranged in a first recess of a wall and attached to the wall of one of the first body structure and the second body structure,
   wherein in the final position the movable element is configured to apply a radial force onto the locking element causing the locking element to bend in the radial direction thereby preventing rotation between the first body structure and the second body structure, and
   wherein the moveable element is configured to axially slide against the locking element as the movable element is moved towards the final position to thereby bend the locking element radially such that it engages with a second recess of a wall of the other one of the first body structure and the second body structure.

2. The locking mechanism as claimed in claim 1, wherein the movable element is a dose indicator configured to provide an indication of the remaining number of doses.

3. The locking mechanism as claimed in claim 1, wherein the locking element is a spring.

4. The locking mechanism as claimed in claim 3, wherein the spring is a sheet spring.

5. The locking mechanism as claimed in claim 1, wherein the spindle and the movable element have a threaded connection.

6. The locking mechanism as claimed in claim 1, wherein the movable element has an elongated axially extending end portion which has a bevelled cross-section, and wherein the locking element has a radially curved section configured to cooperate with the axially extending end portion to thereby cause bending of the locking element.

7. An aerosol dispenser comprising a locking mechanism according to claim 1.

8. The aerosol dispenser as claimed in claim 7, wherein the aerosol dispenser is an inhaler or an eye dispenser.

9. A locking mechanism for an aerosol dispenser, wherein the locking mechanism comprises:
   a first body structure;
   a second body structure rotatably attached to the first body structure;
   a spindle rotatably attached to the second body structure, where the spindle comprises an actuator that is rotationally cooperate with the first body structure such that rotation of the first body structure relative to the second body structure causes rotation of the actuator and of the spindle;
   a dose indicator configured to provide a user an indication of a remaining number of doses and that is arranged around the spindle, where the spindle is rotatable relative to the dose indicator and where rotation of the spindle causes movement of the dose indicator along the spindle from an initial position to a final position;
   a locking element comprising a spring wherein the spring is arranged in a first recess of a wall and attached to the wall of one of the first body structure and the second body structure,
   wherein in the final position the dose indicator will apply a radial force onto the locking element causing the locking element to bend in the radial direction thereby preventing rotation between the first body structure and the second body structure; and wherein the dose indicator axially slides against the spring as the dose indicator moves towards the final position thereby bending the spring radially such that it engages with a second recess of a wall of the other one of the first body structure and the second body structure.

10. The locking mechanism of claim 9, wherein the spindle and the dose indicator are threadedly connected.

11. The locking mechanism of claim 10, wherein the dose indicator has an elongated axially extending end portion having a bevelled cross-section, where the locking element has a radially curved section configured to cooperate with the axially extending end portion to thereby cause bending of the locking element.

12. The locking mechanism of claim 9, wherein the spring is a sheet spring.

* * * * *